(12) United States Patent
Sun et al.

(10) Patent No.: US 7,138,799 B2
(45) Date of Patent: Nov. 21, 2006

(54) METHOD FOR MEASURING ROTATIONAL SPEED OF MOLECULE OF FULLERENES

(75) Inventors: Yong Sun, Iizuka (JP); Tatsuro Miyasato, Kitakyushu (JP)

(73) Assignee: Japan Science and Technology Agency, Saitama (JP)

( * ) Notice: Subject to any disclaimer, the term of this patent is extended or adjusted under 35 U.S.C. 154(b) by 57 days.

(21) Appl. No.: 10/520,042

(22) PCT Filed: Jul. 11, 2003

(86) PCT No.: PCT/JP03/08822

§ 371 (c)(1),
(2), (4) Date: Dec. 30, 2004

(87) PCT Pub. No.: WO2004/008126

PCT Pub. Date: Jan. 22, 2004

(65) Prior Publication Data

US 2006/0066305 A1 Mar. 30, 2006

(30) Foreign Application Priority Data

Jul. 12, 2002 (JP) .............................. 2002-203595

(51) Int. Cl.
*G01V 3/00* (2006.01)
(52) U.S. Cl. .................................... 324/300
(58) Field of Classification Search ..................... None
See application file for complete search history.

(56) References Cited

U.S. PATENT DOCUMENTS 5,640,705 A * 6/1997 Koruga ........................ 588/16
6,017,630 A * 1/2000 Tanaka et al. ............... 428/402
6,830,783 B1 * 12/2004 Fukui et al. ................. 427/475
2002/0025429 A1 * 2/2002 Fukui et al. ................. 428/341
2004/0022958 A1 * 2/2004 Fukui et al. ................. 427/458
2006/0066305 A1 * 3/2006 Sun et al. .................... 324/300

FOREIGN PATENT DOCUMENTS

EP 1536223 A1 * 6/2005
JP 2004045238 * 2/2004
WO WO 2004008126 A1 * 1/2004

OTHER PUBLICATIONS

Son Yu et al., article "Dielectric Loss in C60 Films Observed by Direct Coupling with Electromagnetic Fields" Kyushu Institute of Technology Mar. 2002, vol. 49, No. 2, p. 582. under document identifier 29p-YL-17 0226 on p. 582.*

* cited by examiner

*Primary Examiner*—Diego Gutierrez
*Assistant Examiner*—Tiffany A. Fetzner
(74) *Attorney, Agent, or Firm*—Fay, Sharpe, Fagan, Minnich & McKee, LLP

(57) ABSTRACT

Disclosed is a method for measuring the molecular rotation speed (the number of rotations or the rotation frequency) of a fullerene or a fullerene derivative in a relatively simple and inexpensive manner, for the evaluation of the fullerenes. The method comprises having a thin film of the fullerene or the fullerene derivative absorb an electromagnetic wave varied in frequency, and measuring the change in electromagnetic wave intensity against temperature, thereby determining the molecular rotation speed of the fullerene or the fullerene derivative from the frequency of the electromagnetic wave at the temperature where there is an abrupt change in the electromagnetic wave intensity from the absorption region to the non-absorption region. In a preferred embodiment, electromagnetic waves produced from the surface of a surface acoustic wave device are used.

2 Claims, 2 Drawing Sheets

METHOD FOR MEASURING ROTATIONAL SPEED OF MOLECULE OF FULLERENES

TECHNICAL FIELD

The present invention relates to a method for measuring the molecular rotation speed (the number of rotations or the rotation frequency) of fullerenes in order to evaluate the fullerenes.

BACKGROUND ART

Nanotechnology is viewed as a promising technology with the potential to produce a technology revolution in the twenty-first century. Among leading nanomaterials shouldering the advance of nanotechnology are fullerenes.

Fullerenes are carbonaceous materials in the form of hollow spherical cages typified by $C_{60}$ (Buckminsterfullerene) and have attracted the interest of many scientists as a new research subject since their discovery by Smalley and Kroto in 1985. Attempts have been made to take advantage of the unique structure of fullerenes to develop novel functional materials with various practical applications.

For example, the superconductivity transition temperature of $C_{60}$ crystal is 18K, whereas it was found that $C_{60}$ HBr3, a derivative compound of $C_{60}$, achieves a superconductivity transition temperature as high as 117K. As this temperature is much higher than the temperature of liquid nitrogen, it represents a major step forward in the elucidation of the mechanism by which superconductivity is introduced and the practical application of superconductive materials. In the field of alternative energy resources, the ability of fullerenes to absorb hydrogen is expected to lead to their use as hydrogen-storage materials in fuel cells and for other purposes. In the field of medicine and life science, fullerenes can be used as carriers for new pharmaceutical or efficacious components, because the fullerene molecule, called the Bucky ball, is characterized in being inactive and nontoxic, being so small as to easily interact with cells, proteins, viruses and the like, and being variously modifiable. Thus, fullerenes are being used to develop medicines for combating the AIDS virus, amytrophic lateral sclerosis, osteoporosis and other disorders. A wide range of applications are also being studied in the fields of electronic materials and composite materials. Not only are fullerenes finding applications such as those mentioned above but it has also been pointed out in the environmental field that fullerenes may be contained in exhaust gases. Thus, elucidation of the activity of these nanomolecules is also required from the viewpoint of learning how they influence the environment and the human body.

In contrast to conventionally known general molecules, fullerenes, typified by $C_{60}$, and their derivatives are distinctive from the viewpoint of physical properties in that each molecule rotates as a whole, and it has already been demonstrated that the state or condition of such molecular motion strongly influences the functions exerted by the molecules (R. D. Johnson et al., "$C_{60}$ Rotation in the Solid State-Dynamics of a Faceted Spherical Top" Science, 255, (6), 1235–1238 (1992)). For example, as the interactions among the molecules of fullerenes or their derivatives intensify, the molecular rotation speed (the number of rotations) thereof decreases.

Thus, in developing applications or uses of fullerenes or their derivatives in various fields as mentioned above, it is important to know the molecular rotation speed thereof since it serves as important information for evaluating the fullerenes or their derivatives. A method hitherto reported for measuring the molecular rotation speed of fullerenes or their derivatives utilizes a nuclear magnetic resonance (NMR) apparatus for the measurement (R. Tycko et al., "Molecular Dynamics and the Phase Transition in Solid $C_{60}$" Phys. Rev. Letters, 67, (14), 1886–1889 (1991); R. Tycko et al., "Molecular Orientational Dynamics in Solid $C_{70}$: Investigation by One and Two dimensional Magic Angle Spinning Nuclear Magnetic Resonance" J. Chem. Phys., 99, (19), 7554–7564 (1993)). This method requires an expensive apparatus and since the measurement is destructive, an "in situ" measurement is not possible. In addition, the method is not suitable for evaluating fullerenes in life science and the like since the measurement is carried out in vacuo.

The object of the present invention is to provide a novel method by which the molecular rotation speed of fullerenes or fullerene derivatives can be measured in a relatively simple and inexpensive manner.

DISCLOSURE OF THE INVENTION

The present inventors found that when a fullerene or fullerene derivative is rendered to absorb an electromagnetic wave varied in frequency, there is observed a sharp change in the electromagnetic wave absorption at the temperature where the molecular rotation speed (the number of rotations) of the fullerene or fullerene derivative synchronizes with the frequency of the electromagnetic wave to make electromagnetic wave absorption substantially nil, and that such phenomenon can be utilized in the measurement of the molecular rotation speed (the number of rotations or the rotation frequency).

Thus, according to the present invention there is provided a method for measuring the molecular rotation speed of a fullerene or a fullerene derivative which comprises having a thin film of the fullerene or the fullerene derivative absorb an electromagnetic wave varied in frequency, and measuring the change in electromagnetic wave intensity against temperature, thereby determining the molecular rotation speed of the fullerene or the fullerene derivative from the frequency of the electromagnetic wave at a temperature where there is an abrupt change in the electromagnetic wave intensity from the absorption region to the non-absorption region. As the electromagnetic waves to be employed in the method for measuring a fullerene or a fullerene derivative according to the present invention, it is particularly preferred to use electromagnetic waves produced from the surface of a surface acoustic wave device.

BEST MODE FOR CARRYING OUT THE INVENTION

Figure 1:
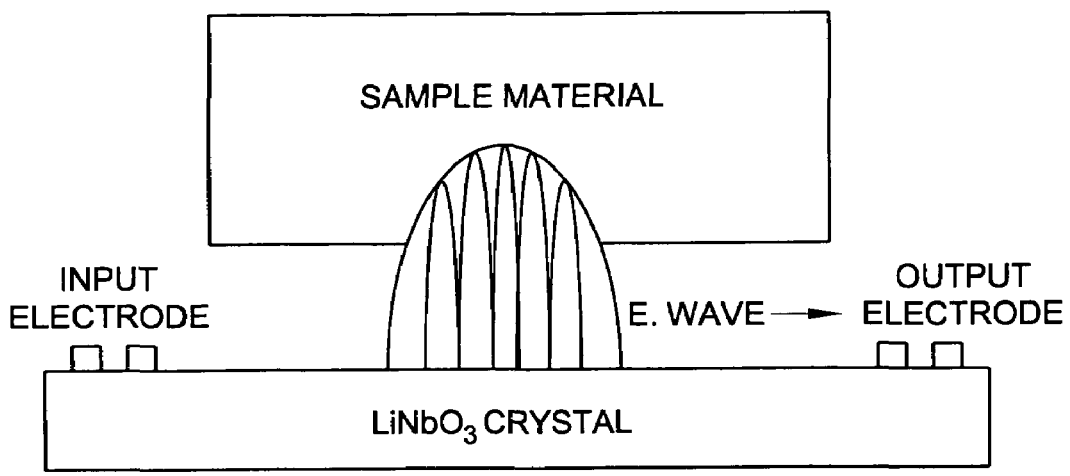
FIG. 1 schematically shows a method of the measurement according to the present invention.

"Fullerene" as termed with respect to the present invention is used as a general term for a carbon allotrope in the shape of a hollow spherical cage typified by C60 but including in addition to $C_{60}$ such other known types as $C_{70}$, $C_{76}$, $C_{78}$, $C_{82}$, $C_{84}$, $C_{90}$ and $C_{96}$. "Fullerene derivative" as termed with respect to the present invention means a derivative obtained by chemical modification of a fullerene as described above, and may be expressed by, for example, the general formula: $C_nM_x$. In this formula, n denotes an integer such as 60, 70, 76, 78, 82, 84, 90, or 96 as can be seen from the above. M represents an atom, a functional group or a molecule attached to the fullerene by chemical modification wherein X denotes a positive integer. In the present specification these fullerenes and fullerene derivatives are sometimes collectively called "fullerenes."

Fullerenes and fullerene derivatives as described in the above perform molecular rotation even at a very low temperature and the rotation speed (the number of rotations) increases as temperature increases. The present inventors discovered that, upon irradiating a thin film of such a fullerene or fullerene derivative with an electromagnetic wave having a specific frequency, the absorption of the electromagnetic wave, occurring at low temperatures, abruptly ceases to be observed beyond a certain temperature.

This can be accounted for as follows: Fullerenes are electrically-conductive like graphite and, at low temperatures, the formation of electrical connections among fullerene molecules can be observed as the absorption of the electromagnetic wave, whereas at higher temperatures the number of molecular rotations of fullerenes is higher than the frequency of the electromagnetic wave thus resulting in no electromagnetic wave absorption. More specifically, at the temperature where the electromagnetic wave intensity changes in an abrupt manner from the absorption region to the non-absorption region, the number of molecular rotations of a fullerene or fullerene derivative synchronizes with the frequency of the electromagnetic wave. The present invention is based on this finding and is directed to ascertaining the molecular rotation speed (the number of rotations or the rotation frequency) of a fullerene or fullerene derivative from the frequency of the electromagnetic wave at that temperature.

Examples of means for causing fullerenes to absorb (for irradiating fullerenes with) an electromagnetic wave include that of bringing the thin film of a fullerene or fullerene derivative into contact with electrodes to which a high frequency is applied. However, this method suffers from low accuracy of electromagnetic wave absorption measurement because of the electrode effect. In another method the measurement is carried out in an electromagnetically shielded room and the reflective wave is analyzed. This method requires a large room in which strong electromagnetic waves must be produced with sophisticated equipment and apparatuses. In addition, by this method it is actually difficult to make an accurate measurement because of various noise factors.

Thus, in accordance with a particularly preferred embodiment of the present invention, as the electromagnetic waves to be absorbed into fullerenes there are used electromagnetic waves produced (leaked) from the surface of a surface acoustic wave device. The surface acoustic wave device is a well known device having two interdigital electrodes (transducers) mounted on the surface of piezoelectric crystal such as crystallized quartz or $LiNbO_3$. On applying a voltage to one of the electrodes, there is produced a surface acoustic wave (SAW) on the surface of the piezoelectric crystal, which wave is then received by the other electrode to induce an electromotive force therein. With this device it is easy to alter the frequency of the electromagnetic wave (surface acoustic wave) through appropriate design of the shape of the electrodes.

In carrying out the present invention, it suffices simply to use a surface acoustic wave device and place a sample material (specimen) of e.g. a fullerene in parallel with the surface of the piezoelectric crystal. Thus, a portion of the SAW transmitted between the electrodes on the surface of the piezoelectric crystal is absorbed into the sample material, and it is possible to determine the attenuation of the electromagnetic wave from the output/input ratio of the electromagnetic wave intensity. Since the sample material is not in contact with the electrodes, accurate measurement of change in the electromagnetic wave intensity can be ensured using measurement equipment that is easy to fabricate or readily available.

An example is given in the following to explain the characteristic features of the present invention in a more concrete manner, but this example is not for restricting the present invention.

EXAMPLE

Measurements were conducted on $C_{60}$ fullerene, $C_{70}$ fullerene, carbon nanotube and graphite crystal utilizing electromagnetic waves produced from the surface of a surface acoustic wave device.

FIG. 1 conceptually shows the principle of measurement. Through an input electrode mounted on $LiNbO_3$ piezoelectric crystal (10 mm×30 mm) having a thickness of 0.5 mm, was input a pulsating electromagnetic wave (width: 800 ns) with a certain frequency. The pulsating wave is transmitted on the surface of the crystal and recovered into the output electrode. Frequencies employed are 50, 150, 200, 250, 350 and 450 MHz.

A sample material is placed in parallel with the surface of the crystal and thus the electromagnetic wave is attenuated by being absorbed into the sample material. The degree of the attenuation is determined from the output/input ratio in the electromagnetic wave intensity. The measurements were carried in the temperature range of 15K to 350K.

$C_{60}$ and $C_{70}$ were each deposited on a silicone substrate to form a thin film of approx. 0.5 μm in thickness. The carbon nanotube was grown on a silicon carbide crystal to form a film of approx. 1 μm thickness. The graphite used was a highly oriented pyrolytic graphite. The size of each sample material was approx. 10 mm×15 mm×1 mm.

Figure 2:
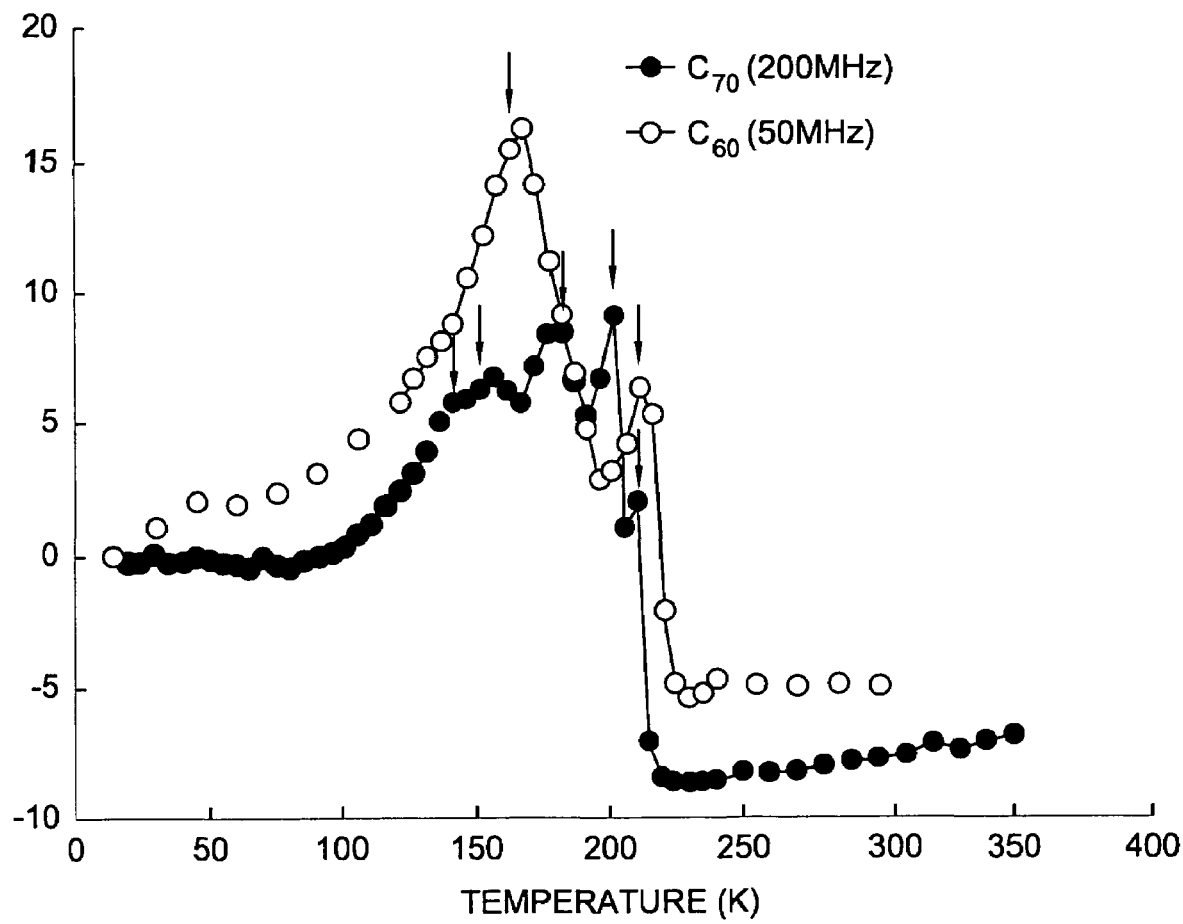
FIG. 2 shows electromagnetic wave absorption characteristics of $C_{60}$ and $C_{70}$ on which measurement was carried out in accordance with the present invention.

FIG. 2 shows electromagnetic wave absorption characteristics measured for $C_{60}$ and $C_{70}$ thin films. The $C_{60}$ thin film and the $C_{70}$ thin film indicated a similar tendency, and a steep drop was observed at around 240K at which there was an abrupt change in the electromagnetic wave absorption. The background difference sandwiching the steep drop is accounted for by the Joule loss inside the fullerene molecules due to the electromagnetic wave absorption. At a low temperature in the region on the left side of the steep drop, the number of molecular rotations (molecular rotation speed) of the fullerenes is lower than the frequency of the electromagnetic wave, thus forming the electric connections between the fullerene molecules and the electromagnetic wave, which can be observed as the absorption: The electromagnetic wave attenuation is in a positive region in FIG. 2. On the other hand, at a high temperature in the region on the right side of the steep drop, the number of molecular rotations of the fullerene is higher than the frequency of the electromagnetic wave, and hence no absorption is observed. The electromagnetic wave attenuation is in a negative region in FIG. 2.

At a temperature around the steep drop where the electromagnetic wave intensity abruptly changes from the absorption region to the non-absorption region, the molecular rotation speed of the fullerene molecules synchronizes with the frequency of the electromagnetic wave, and the rotation frequency (the number of rotations or the rotation speed) of the fullerene molecules can be obtained from the frequency of the electromagnetic wave at that temperature. Thus, in the case as shown by FIG. 2, the number of molecular rotations of $C_{60}$ is 50 MHz and the number of molecular rotations of $C_{70}$ is 200 MHz, at around 240K.

It is worth noting that the peaks observed at the low temperature region are due to the relaxation absorption of the dipoles formed between the fullerene molecules and the oxygen atoms chemically bonded to $C_{60}$ or $C_{70}$ molecules. The number of the absorption peaks depends upon the types of bonding of the individual fullerene structures: two peaks being observed for $C_{60}$ and five peaks for $C_{70}$. The fact that relaxation absorption of the dipoles formed between fullerene molecules and oxygen atoms occurs is conventional knowledge. Measurement of such peaks is not a direct object of the present invention.

Figure 3:
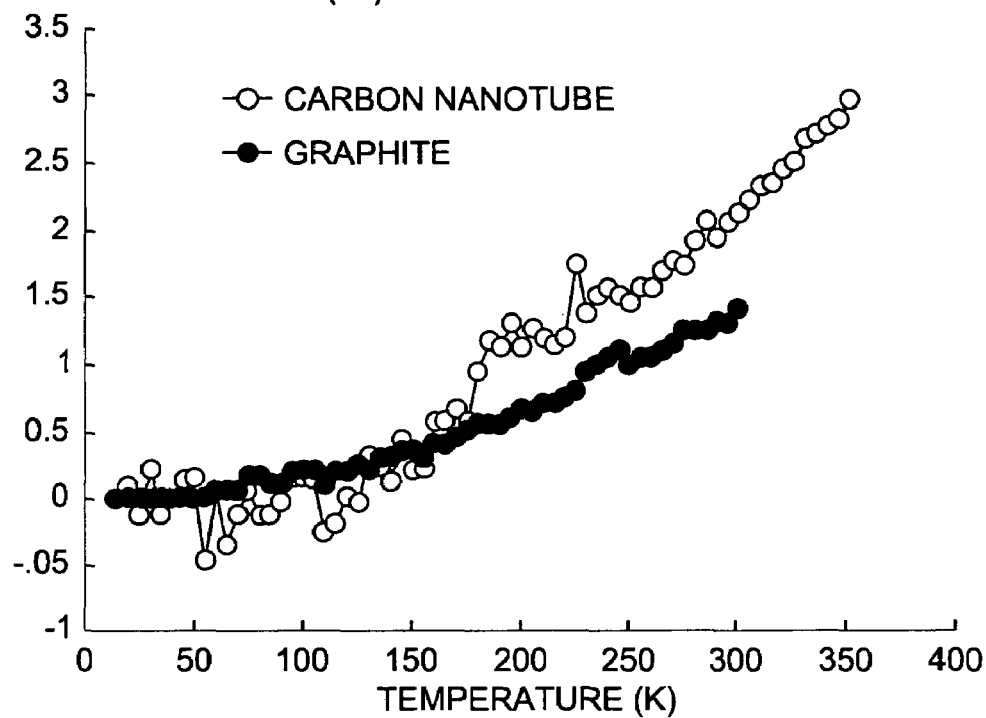
FIG. 3 shows electromagnetic wave absorption characteristics of a graphite crystal and a carbon nanotube on which measurement was made for comparison.
Figure 4:
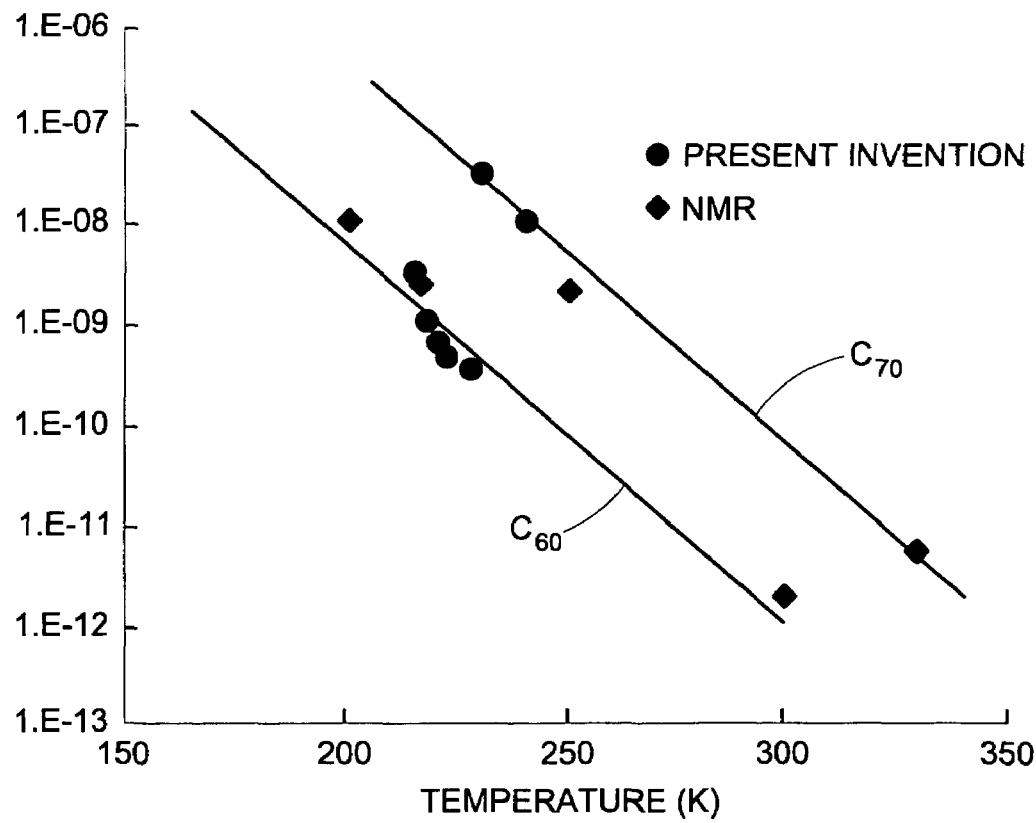
FIG. 4 shows the results of the measurements of the molecular rotation frequencies of $C_{60}$ and $C_{70}$ by the present invention, in comparison with those by the nuclear magnetic resonance method.

FIG. 3 shows electromagnetic wave absorption characteristics of the graphite crystal and the carbon nanotube film measured in the same manner as explained in the foregoing. Graphite or carbon nanotube resembles $C_{60}$ or $C_{70}$ in the bonding state among carbon atoms but does not perform a molecular rotation motion. Thus, with the graphite crystal and the carbon nanotube film there is observed no steep drop as seen in the case of $C_{60}$ or $C_{70}$. The electromagnetic wave absorption exhibits a gradual increase with increasing temperature, which reflects the temperature-dependency of the conductivity of the graphite crystal or the carbon nanotube film. Thus, the method of the present invention is useful for detecting the molecular rotation inherent in fullerenes, and for determining the rotation speed (the number of rotations or the rotation frequency) thereof FIG. 4 shows the results of the measurements of molecular rotation speed (rotation frequency) of $C_{60}$ and $C_{70}$ by the present invention in comparison with those by nuclear magnetic resonance (NMR). The results obtained by the method of the present invention are in fair agreement with those obtained by the conventional nuclear magnetic resonance method.

INDUSTRIAL UTILITY

As apparent from the foregoing, the present invention enables the evaluation of fullerenes, which are expected to have applications as functional materials, by making good use of electromagnetic waves to detect the molecular rotation motion of the fullerenes and to determine the rotation speed (the number of rotations or the rotation frequency) thereof. The measurement is nondestructive because of utilization of electromagnetic waves. The method can be done under atmospheric conditions, enabling "in situ" measurement, for example, in a case where fullerenes are applied to living bodies or the like. In addition, a surface acoustic wave device, which is a particularly preferred device for carrying out the method of the present invention, is not costly and is compact and portable. What is more, the measurement by the present invention is as accurate as that by the nuclear magnetic resonance method which is costly and sophisticated.

The invention claimed is:

1. A method for measuring the molecular rotation speed of a fullerene or a fullerene derivative which comprises having a thin film of the fullerene or the fullerene derivative absorb an electromagnetic wave varied in frequency, and measuring the change in electromagnetic wave intensity against temperature, thereby determining the molecular rotation speed of the fullerene or the fullerene derivative from the frequency of the electromagnetic wave at a temperature where there is an abrupt change in the electromagnetic wave intensity from the absorption region to the non-absorption region.

2. The method for measuring the molecular rotation speed of a fullerene or a fullerene derivative according to claim 1, wherein electromagnetic waves produced from the surface of a surface acoustic wave device are used.

* * * * *